United States Patent
TETS et al.

(10) Patent No.: US 8,999,959 B2
(45) Date of Patent: Apr. 7, 2015

(54) DRUG FOR TREATING LIVER LESIONS CAUSED BY THE ACTION OF CHEMICAL OR BIOLOGICAL AGENTS

(75) Inventors: Viktor Veniaminovich TETS, Saint-Petersburg (RU); Georgy Viktorovich TETS, Saint-Petersburg (RU); Konstantin Andreevich Krasnov, Saint-Petersburg (RU)

(73) Assignees: Viktor Veniaminovich TETS, Saint Petersburg (RU); Georgy Viktorovich TETS, Saint Petersburg (RU)

( * ) Notice: Subject to any disclaimer, the term of this patent is extended or adjusted under 35 U.S.C. 154(b) by 0 days.

(21) Appl. No.: 13/883,854

(22) PCT Filed: Oct. 10, 2011

(86) PCT No.: PCT/RU2011/000792
§ 371 (c)(1), (2), (4) Date: May 7, 2013

(87) PCT Pub. No.: WO2012/064221
PCT Pub. Date: May 18, 2012

(65) Prior Publication Data
US 2013/0237704 A1    Sep. 12, 2013

(30) Foreign Application Priority Data
Nov. 8, 2010 (RU) .................. 2010145439

(51) Int. Cl.
| | | |
|---|---|---|
| A61K 31/675 | (2006.01) | |
| C07D 239/02 | (2006.01) | |
| C07D 239/22 | (2006.01) | |
| A61K 31/513 | (2006.01) | |

(52) U.S. Cl.
CPC ............ *C07D 239/22* (2013.01); *A61K 31/513* (2013.01)

(58) Field of Classification Search
CPC .................................................. C07D 239/02
See application file for complete search history.

(56) References Cited

U.S. PATENT DOCUMENTS

| | | | |
|---|---|---|---|
| 6,624,202 | B2 | 9/2003 | Smith et al. |
| 7,074,925 | B1 | 7/2006 | Ashkinazi |
| 2002/0173521 | A1 | 11/2002 | Smith et al. |
| 2004/0106654 | A1 | 6/2004 | Smith et al. |

FOREIGN PATENT DOCUMENTS

| | | |
|---|---|---|
| EP | 1 083 172 | 3/2001 |
| EP | 1083172 A1 * | 3/2001 |
| RU | 2 188 196 | 8/2002 |
| RU | 2003 103 291 | 1/2005 |
| WO | 99/61427 | 12/1999 |

OTHER PUBLICATIONS

March, J. "Advanced Organic Chemistry: Reactions, Mechanisms, and Structure." 4th ed. Copyright 1992, pp. 72-73.*
Pankratov A. N. Kisloty i osnovaniya v khimii: Ushebnoe posobie v kontekste nauchnogo napravleniya, 2009, Saratov, 32 p, especially p. 25.
J.A. Bonacin, et al. "Vibrational spectra and theoretical studies of tautomerism and hydrogen bonding in the violuric acid and 6-amino-5-nitrosouracil system", Vibrational Spectroscopy, 2007, vol. 44, No. 1, pp. 133-141.
European Search Report dated Feb. 19, 2014, from corresponding European Application No. EP11839641.5.
E.E. Frezza, et al. "Sex hormones and trace elements in rat CCL4-induced cirrhosis and hepatocellular carcinoma", European Journal of Cancer Prevention, 1993, vol. 2, pp. 357-359.
Gornostaev L.M. "Tautomeriya organicheskikh soedinenii" (The Tautomerism in Organic Chemistry), Sorosovkii Orbazovatelnyi zhurnal (Soros Educational Journal), 1996, No. 4, pp. 33-38.
Translation of International Preliminary Report on Patentability dated May 14, 2013, from corresponding International Application No. PCT/RU2011/000792.
Translation of International Search Report dated Feb. 2, 2012, from corresponding International Application No. PCT/RU2011/000792.
Translation of the Written Opinion of the International Searching Authority dated Jan. 26, 2012, from corresponding International Application No. PCT/RU2011/000792.

* cited by examiner

*Primary Examiner* — Andrew D Kosar
*Assistant Examiner* — John S Kenyon
(74) *Attorney, Agent, or Firm* — Troutman Sanders LLP

(57) ABSTRACT

The invention relates to medicine and can be used for treating liver lesions caused by chemical or biological agents. The drug for treating liver lesions caused by chemical or biological agents is embodied as 1-(4-bromophenyl)-6-hydroxy-5-nitroso-1,2,3,4-tetrahydropyrimidine-2.4-dione: (I), or salts thereof having the general formula: (II), where X is selected from $Na^+$, $K^+$, $Li^+$, $NH_4^+$, $NH_2CONH_3^+$ or another pharmacologically acceptable cation. The effectiveness of the preparation in treating liver diseases of different etiologies is increased.

20 Claims, No Drawings

DRUG FOR TREATING LIVER LESIONS CAUSED BY THE ACTION OF CHEMICAL OR BIOLOGICAL AGENTS

CROSS REFERENCE TO RELATED APPLICATIONS

This application is a U.S. National Phase Application under 35 U.S.C. §371 of International Patent Application PCT/RU2011/000792 filed Oct. 10, 2011, which claims priority to Russian Patent Application No. 2010145439 filed Nov. 8, 2010. The International Application was published on May 18, 2012, as International Publication No. WO 2012/064221A1 under PCT Article 21(2). The entire contents of these applications are hereby incorporated by reference.

TECHNICAL FIELD

The invention relates to medicine and can be used for treating liver lesions caused by chemical or biological agents.

BACKGROUND ART

Known drugs for treating liver lesions are based on organic agents of natural or synthetic origin, e.g. "Essentiale", which contains Essential Phospholipids as an active ingredient. Another known drug "Legalon" ("Carsil"), intended for treating liver diseases, is produced on the basis of milk thistle fruit extract. Yet another drug for treating liver diseases is known—the preparation "Prostenonum", see RU 1821209 A1.

Essentiale has been taken as a prototype of the present invention.

The studies showed that although the prototype has a certain hepatoprotective effect, the level of this effect is relatively low. Active substances of Essentiale preparation are phospholipids, which are found in many food products and do not constitute an agent with a pronounced curative effect.

SUMMARY OF THE INVENTION

It is an object of the present invention to increase the effectiveness of the preparation for treating liver diseases of different etiologies.

According to the invention the drug for treating liver lesions caused by chemical or biological agents is embodied as 1-(4-bromophenyl)-6-hydroxy-5-nitroso-1,2,3,4-tetrahydropyrimidine-2.4-dione:

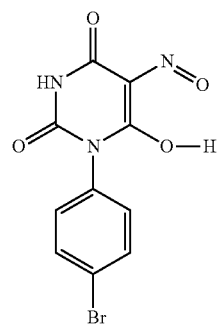 [SMILES: O=Nc1c(O)n(-c2ccc(Br)cc2)c(=O)[nH]c1=O]

or salts thereof having the general formula:

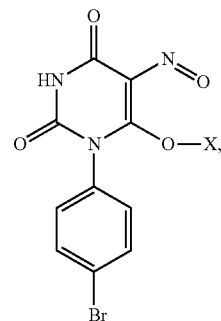

where X is selected from $Na^+$, $K^+$, $Li^+$, $NH_4^+$, $NH_2CONH_3^+$ or another pharmacologically acceptable cation.

The applicant has not found any sources of information containing data on technical solutions identical to the present invention, which enables to conclude that the invention conforms to the criterion "Novelty" (N).

The applicant has not found any sources of information containing data on the influence of the features of the invention on the technical result produced by the invention, which consists in virtually complete and reliable normalization of the condition and functions of liver. In applicant's opinion, this enables to conclude that the present technical solution conforms to the criterion "Inventive Step" (IS).

BRIEF DESCRIPTION OF THE DRAWINGS

The invention is further explained, by way of detailed description of examples of its embodiments, without reference to any drawings.

PREFERRED EMBODIMENT

The inventive substance is produced as follows.

At the first stage of synthesis of the preparation, 1 mol (172 g) of 4-bromoaniline (1) is dissolved while heating to 50° C. in 2.5 l of water with the addition of 1.1 mol of HCL (105 ml) 30% hydrochloric acid.

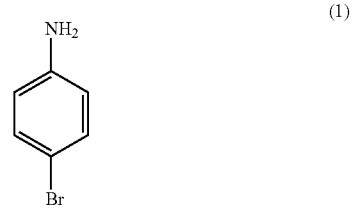

Then a solution of 1.1 mol (81 g) of potassium cyanate in 400 ml of water is poured to the abovementioned solution while stirring. The obtained mixture is heated at a water bath for 15 min and then cooled, after which white crystal precipitate is separated and washed with water, then with aqueous alcohol, after which the precipitate is air-dried at 50° C. until reaching constant weight. 175 g of the product (2) is obtained: N-(4-bromophenyl) urea.

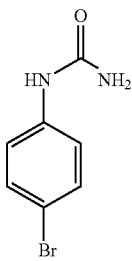

(2)

Then, at the second stage of synthesis, 2 mol (46 g) of sodium metal are dissolved in 600 ml of anhydrous methanol. 1 mol (160 g) of diethyl malonic ether is added to the obtained solution and stirred for 5 minutes. Then 1 mol (215 g) of N-(4-bromophenyl) urea (2) is added and the resulting mixture is boiled for 6 h under reflux while stirring. Then the mixture is cooled down to 25° C. and 3 l of cold water are added thereto, after which it is sustained for 10 min, and then the solution is filtered out from the residue. Then a solution of 75 g (1.1 mol) of sodium nitrite in 400 ml of water is poured into the obtained clear solution and stirred. The solution is cooled down to 10° C., then 2.2 mol (132 g) of acetic acid are added dropwise while stirring, and then the solution is sustained at 25° C. for 1 hour. Then 400 ml of 30% hydrochloric acid are added to the obtained mixture and stirred for 10 minutes. The formed precipitate is filtered, washed with 1% solution of HCl, then with water, and then dried. The obtained product is recrystallized from 3 l of alcohol. 248 g of final product are obtained (1-(4-bromophenyl)-6-hydroxy-5-nitroso-1,2,3,4-tetrahydropyrimidine-2.4-dione) (3) having melting temperature of 220° C. (with decomposition).

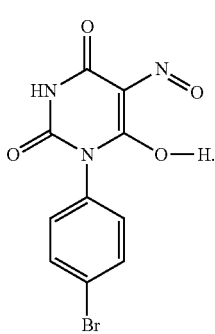

(3)

In order to obtain salts of 1-(4-bromophenyl)-6-hydroxy-5-nitroso-1,2,3,4-tetrahydropyrimidine-2.4-dione, 1 g of this substance is dissolved in 20 ml of water with the addition of corresponding base: NaOH, KOH, LiOH, NH$_4$OH, NH$_2$CONH$_2$ or another base containing pharmacologically acceptable cation, e.g. guanidine, monoethanolamine etc. The obtained solution is stripped to dryness in vacuum.

The obtained agent can be applied using pharmacologically acceptable fillers, adjuvants and transporters, such as polyvinylpyrrolidone (PVP), methylcellulose (MC), oxypropylmethylcellulose (OPMC), carboxymethylcellulose (CMC), sodium-carboxymethylcellulose (Na-CMC) and certain other substances, corn starch, talcum, kaolin, bentonites, aerosil, beet sugar, milk sugar, sodium chloride, sodium hydrocarbonate, aluminum oxide, aluminum stearate, lecithin, serum proteins, phosphates, glycine, sorbic acid, potassium sorbate, mixture of glycerides of saturated vegetable fatty acids, salts of zinc, colloid silicon dioxide, trisilicate of magnesium, lanoline etc.

The inventive substance can be administered orally, parenterally, by means of a spray, locally, through rectum, nasally, lingually, vaginally or by means of implants.

We consider it best to administer the preparation orally, via injections or suppositories. The term "parenterally" in this context means the following: subdermally, intradermally, intravenously, intramuscularly.

Pharmacological preparations based on the invention can be embodied as a sterile preparation for injections, both as an aqueous solution or an oil suspension. The suspension can be created by means of a common known method employed for producing such form of drugs, using any suitable detergents and other auxiliary substances (Tween 80). The sterile preparation for injections can be embodied both as a solution or a suspension, wherein any nontoxic parenterally acceptable substance, e.g. 1.3-butanediol, can be used as a solvent or liquid base for said solution or suspension. Mannitol, water, Ringer's solution and isotonic solution of sodium chloride can be used as acceptable solvents. An oily solution can be created by means of non-volatile vegetable oils that are traditionally used for obtaining oily solutions and suspensions. Any neutral non-volatile oil is suitable for this purpose, as well as synthetic mono- and diglycerides, and fatty acids. Injection preparations can be created by means of oleic acid, glycerides, olive or castor oil, in particular their polyoxyethylated derivatives, since these constitute natural pharmacologically acceptable vegetable oils. Oily solutions and suspensions can also comprise stabilizers and detergents in the form of long-chain alcohols or other similar substances.

Pharmacological preparations based on the inventive substance can be administered orally, in a dosage and form that is acceptable for oral administration, including capsules, pills, aqueous solutions and suspensions. For pills, lactose and corn starch are usually used as fillers, and process additives such as magnesium stearate are also added. If the preparation for oral administration is manufactured as a capsule, then lactose and corn starch are used as fillers. If the drug is manufactured as an aqueous suspension, then emulsifiers and stabilizers are also added to the active substance. If necessary, substances providing the preparation with taste, odor and color can also be added.

Pharmacological preparations can also be manufactured in the form of suppositories for rectal or vaginal administration. These drug forms can be manufactured by mixing the inventive substance with a suitable non-irritant filler that remains hard in room temperature and becomes soft in rectal or vaginal temperature. Cocoa butter, beeswax and polyethylene glycols can be used as said fillers.

In pharmacological preparations intended for local skin application, the active substance should be combined with a suitable ointment base that can contain the active substance in dissolved form or as a suspension. Said ointment base can include mineral oils, liquid petrolatum, white petrolatum, propylene glycol, a mixture of polyoxyethylene and polyoxypropylene, emulsifying wax and water. Pharmacological preparations intended for external use can also be based on a lotion or cream, which contains the active substance in the form of a solution or suspension. In this case the fillers can be embodied as a mineral oil, sorbitan monostearate, Polysorbate 60, cetyl ethers, wax, cetearyl alcohol, 2-octyldodecanol, benzyl alcohol, water and other suitable ingredients.

The inventive substance can also be used for manufacturing such medical products for external use as plasters, nasal sprays or inhalers. Such products can be manufactured by means of existing technologies used in manufacture of such products. Liquid phase for dissolving the substance can be embodied as isotonic solution of sodium chloride (physiological solution); stabilizer can be embodied as benzyl alcohol or any other suitable substance; absorption activator can be embodied as fluorocarbons in order to increase the bioavailability; dissolution and dispersion can be improved by using any known auxiliary substances used in manufacture of such pharmacological products.

Medical preparations prepared on the basis of the inventive substance can be used in doses from 0.01 to 25 mg of the active substance per 1 kg of patient weight per 24 hours.

Prolonged forms with boosted action of the active substance can be manufactured on the basis of prepared liposomal forms or complexes with polylactic acid.

Biological activity of preparations manufactured on the basis of 1-(4-bromophenyl)-6-hydroxy-5-nitroso-1,2,3,4-tetrahydropyrimidine-2,4-dione or salts thereof is illustrated by the examples provided below. The following is based on the fact that the mechanisms of hepatoxicity—inflammation, cytolysis and cholestasis—are universal and non-specific whatever the agent that induces the liver lesion [Frezza E. E. et al. Sex hormones and trace elements in rat $CCl_4$-induced cirrhosis and hepatocellular carcinoma.—European Journal of Cancer Prevention. 2(4), 357-359, 1993; Lin S. C. et al. Hepatoprotective effects of Taiwan folk medicine: Ixeris chinensis (Thunb.) Nak on experimental liver injuries.—American Journal of Chinese Medicine. 22(3-4), 243-54, 1994.]. Therefore, damage to liver cells is similar for hepatitis caused by various viruses (viruses of hepatitis A, E, B, D, C and some others that are not completely identified yet), bacteria of *Leptospira* genus, chemical exposure at industrial facilities or as a result of poisonous substances that find their way into water or food products, as well as those caused by the effects of alcohol, certain medicines, e.g. cytostatic drugs, as well as exposure to radiation.

Example 1

Treatment of toxic hepatitis by means of parenteral administration of the inventive substance. Acute toxic hepatitis was induced in rats by means of intragastric administration of 50% solution of carbon tetrachloride ($CCl_4$) in olive oil in the amount of 1 ml/kg during 6 days. After 10 days the presence of toxic hepatitis was confirmed by morphological image of liver in all experimental animals. Starting from that day, for 10 days the preparations were administered to the experimental animals by way of treatment, once every 24 hours.

Essentiale was used as the preparation for comparison, which was administered in ampoules in the amount of 1 ml/100 g intravenously, slowly, into the caudal vein. The inventive substance was also administered intravenously in varying amounts in order to refine the treatment procedure. The effectiveness of treatment was evaluated on the basis of clinical performance, body weight dynamics, relative liver mass, the contents of bilirubin, transaminases, phosphatases, ceruloplasmin, total protein, blood serum lipids, the contents of glycogen, glutathione, SH-groups, stress tests (hexenal test, bromsulphalein test) and the histological pattern of liver.

Weight dynamics of the rats were determined by means of scales VLR-500. Liver of the animals was weighted using electronic scales 1602 MP by "Sartorius". The contents of reduced glutathione in liver and the content of sulfhydryl groups in blood serum was evaluated by amperometric titration according to Rubinnaya N. S. (Stalnaya I.D., Garishvili T. G Modern methods in biochemistry. Moscow, Meditsina, 1977, pp. 66-68), the contents of glycogen—by the Samodi method (Stalnaya I.D., Garishvili T. G Modern methods in biochemistry. Moscow, Meditsina, 1977, pp. 66-68). The antitoxic function of liver was evaluated by the duration of hexenal sleep (70 mg per 1 kg of body weight), and the excretory function of liver was assessed by means of bromsulphalein test.

Blood for biochemical tests was obtained by means of paracentesis of the caudal vein of rats.

The activity of ALT, AST, ALP, ACP, LDH, thymol test, the contents of total protein and lipids, cholesterol, blood serum bilirubin were assessed by means of sets Bio-Lat-Test manufactured by a Czech company "Lachema", the contents of ceruloplasmin were assessed according to Babenko (Laboratory research methods in clinical practice. Reference book, under the editorship of V. V. Menshikov. Moscow, Russia—Meditsina, 1987, p. 365). The animals were killed by decapitation, subjected to anatomicopathological autopsy and histological study. The experimental and reference rats were killed by means of decapitation. The material was fixed in 10-15% formaldehyde and embedded in paraffin. Paraffin slices were stained by means of hematoxylin and eosin. Fixed frozen slices were stained for fat by means of Sudan III.

Statistical processing of the experiments' results was done according to Student's T-distribution and F-distribution.

The effectiveness of preparations was assessed according to several groups of indices: morphometric, biochemical and functional. First of all the clinical performance of intoxication was observed. The clinical performance in the group of rats that received $CCl_4$ with no treatment was characterized by hypodynamia, dormancy, disheveled hair and untidy appearance of the animals. They gained weight less well than the other rats. In this group, by day 15 of the study 80% of animals were dead.

In the experimental groups, by the start of treatment (day 10 of the study) 40% of the animals were dead. By the end of the treatment (day 20) the percentage of deaths in the groups was as follows: Essentiale—50%; the inventive substance in the dosage of 25 mg/kg—40%. The application of the inventive substance reduced or almost completely arrested the manifestations of intoxication. These data were confirmed by the results of objective analyses (see Table 1).

Intoxication by carbon tetrachloride was found to be accompanied by reduction of body weight and the increase of relative liver mass. The treatment normalized these characteristics.

This was also confirmed by the results of histological studies. In said experimental conditions the influence of $CCl_4$ caused profound damage to hepatocytes in the liver of experimental rats in the form of steatosis and proteinosis. Large droplets of fat completely filled the cytoplasm of hepatocytes. The macrovesicular steatosis had diffuse form. Only a small number of hepatocytes did not contain fat and had homogeneous cytoplasm. Large vacuoles could be seen in the paraffin preparations at the site of fat inclusions. Cytoplasm of a small part of hepatocytes had intense eosin staining. A part of rats, in addition to said changes, also manifested small foci of necrobiosis; hepatocytes in these areas were pale with indiscernible cellular borders, with no nuclei. Nuclei of most hepatocytes were swollen, cleared, with hyperchromatism of the nuclear membrane.

The majority of treated rats had no degenerative changes of the liver. Trabecular constitution of the liver manifested no abnormalities. Borders of hepatocytes were well-defined. The nuclei contained enough chromatin. Fat test using Sudan III was negative for the majority of rats. In 4 cases of rats treated with Essentiale there was focal microvesicular steatosis.

Thus the inventive substance demonstrated hepatoprotective action thereof on the model of toxic hepatitis caused by carbon tetrachloride. The indices illustrating the condition and function of the liver are shown in tables 2 and 3.

Thus, the conducted studies showed that the inventive substance has hepatoprotective action and surpasses the prototype Essentiale in a series of parameters, in particular, the absence of microvesicular focal steatosis (which was observed in 4 cases of treatment with Essentiale), and the data of marker biochemical and functional indices.

Example 2

Treatment of liver cirrhosis by oral administration of the inventive substance. Liver cirrhosis was induced in rats by means of intragastric administration of 50% solution of carbon tetrachloride ($CCl_4$) in olive oil in the amount of 1 ml/kg during 10 days. After 20 days the presence of liver cirrhosis was confirmed by morphological image of liver in all laboratory animals. Starting from that day, for 10 days the inventive agent was administered to the laboratory animals by way of treatment, once every 24 hours, in varying amounts in order to refine the optimal treatment procedure.

The effectiveness of the inventive preparation was evaluated in comparison with Essentiale by several groups of indices: morphometric, biochemical and functional. First of all the clinical performance of intoxication was observed. The clinical performance in the group of rats that received $CCl_4$ with no treatment was characterized by hypodynamia, dormancy, disheveled hair and untidy appearance of the animals. They gained weight less well than the other rats. In this group by day 15 of the study 80% of the animals were dead, in the group that received Essentiale—60%, in the group that received the inventive agent—40%.

The application of the inventive agent reduced or almost completely arrested the manifestations of intoxication. These data were confirmed by the results of objective analyses (see Table 4).

Intoxication by carbon tetrachloride was found to be accompanied by reduction of body weight and the increase of relative liver mass. The treatment with the inventive agent normalized these characteristics.

This was also confirmed by the results of histological studies. In said experimental conditions the influence of CC14 caused profound damage to hepatocytes in the liver of experimental rats in the form of steatosis and proteinosis. Large droplets of fat completely filled the cytoplasm of hepatocytes. The macrovesicular steatosis had diffuse form. Only a small number of hepatocytes did not contain fat and had homogeneous cytoplasm. Large vacuoles could be seen in the paraffin preparations at the site of fat inclusions. Cytoplasm of a small number of hepatocytes had intense eosin staining. A part of rats, in addition to said changes, manifested small foci of necrobiosis; hepatocytes in these areas were pale with indiscernible cellular borders, with no nuclei. The nuclei of most hepatocytes were swollen, cleared, with hyperchromatism of the nuclear membrane.

The majority of rats treated with the inventive substance had no degenerative changes of the liver. Trabecular constitution of the liver manifested no abnormalities. Borders of hepatocytes were well-defined. Nuclei contained enough chromatin. Fat test using Sudan III was negative for the majority of rats. In 2 cases of rats treated with Essentiale there was focal microvesicular steatosis.

$CCl_4$ intoxication disturbed all functions of the liver: protein-synthetic, detoxicating, lipo-synthetic, which was accompanied by biochemical signs of cytolysis. The activity of transaminases, phosphatases in blood was increased, the contents of total protein, lipids, reserve of sulfhydryl groups in blood serum were reduced, the levels of bilirubin and ceruloplasmin were increased. The reserve of glycogen and reduced glutathione, and the levels of detoxicating cytochromes in liver were reduced. Liver lesions were accompanied with decrease of its functional activity: the duration of hexenal sleep was greatly increased, the excretion of bromsulphalein was slowed down.

Application of the inventive substance virtually completely and reliably normalized the condition and function of liver. Quantitative assessment of the preparation's effectiveness in treatment of toxic hepatitis was performed using a point rating system, taking into account the marker indices: the largest score for each index was assigned to the group with the more pronounced positive effect of the preparation.

Thus the tested substance showed hepatoprotective action that surpassed that of the preparation used for comparison.

INDUSTRIAL APPLICABILITY

The invention can be implemented by means of known materials and equipment. In applicant's opinion, this enables to conclude that the invention conforms to the criterion "Industrial Applicability" (IA).

TABLE 1

Body weight and relative liver mass of experimental animals after treatment of $CCl_4$ intoxication with varying dosages, M ± m.

| | | $CCl_4$ intoxication | | |
| --- | --- | --- | --- | --- |
| Indicators | Intact | No treatment | Essentiale | The inventive substance 25 mg/kg |
| Body weight, g | 179 ± 7 | 165 ± 10* | 176 ± 8 | 174 ± 8 |
| Relative liver mass, g/kg | 29.70 ± 1.46 | 41.30 ± 1.17* | 32.78 ± 1.91 | 27.87 ± 1.03 |

*statistically significant differences from intact animals at $p < 0.05$

TABLE 2

Marker biochemical and functional indices of liver condition of the experimental animals after treatment of $CCl_4$ intoxication with the inventive substance in varying dosages, M ± m.

| | | $CCl_4$ intoxication | | |
| --- | --- | --- | --- | --- |
| Indicators | Intact | No treatment | Essentiale | The inventive substance, 25 mg/kg |
| Alanine aminotransferase, serum, μmol/(s · l) | 0.59 ± 0.04 | 1.56 ± 0.11* | 0.93 ± 0.08* | 0.85 ± 0.08 |

TABLE 2-continued

Marker biochemical and functional indices of liver condition of the experimental animals after treatment of $CCl_4$ intoxication with the inventive substance in varying dosages, M ± m.

| Indicators | Intact | $CCl_4$ intoxication | | |
|---|---|---|---|---|
| | | No treatment | Essentiale | The inventive substance, 25 mg/kg |
| Aspartate aminotransferase, serum, μmol/(s · l) | 0.35 ± 0.04 | 0.80 ± 0.07* | 0.42 ± 0.06 | 0.32 ± 0.04 |
| Alkaline phosphatase, serum, nmol/(s · l) | 852 ± 30.7 | 1677 ± 168.8* | 1070 ± 98.3* | 811 ± 26.3 |
| Hexenal sleep, min | 31.0 ± 2.0 | 59.0 ± 4.0* | 36.0 ± 2.5 | 31.0 ± 2.0 |

*statistically significant differences from intact animals at $p < 0.05$

TABLE 3

Secondary biochemical and functional indices of liver condition of the experimental animals after treatment of $CCl_4$ intoxication with the inventive substance in varying dosages, M ± m.

| Indicators | Intact | $CCl_4$ intoxication | | |
|---|---|---|---|---|
| | | No treatment | Essentiale | The inventive substance, 25 mg/kg |
| Total protein, serum, g/l | 64 ± 2 | 31 ± 4* | 63 ± 5 | 69 ± 6 |
| Total lipids, serum, g/l | 3.5 ± 0.3 | 2.5 ± 0.3* | 3.6 ± 0.09 | 3.4 ± 0.09 |
| ACP, μkat/l | 0.76 ± 0.11 | 2.27 ± 0.19* | 0.71 ± 0.12 | 0.75 ± 0.10 |
| LDH, mmol/h/l | 4.94 ± 0.32 | 8.48 ± 0.36* | 4.73 ± 0.30 | 5.49 ± 0.45 |
| Thymol test, turbidity units | 1.46 ± 0.03 | 5.99 ± 0.35* | 1.40 ± 0.11 | 1.18 ± 0.17 |
| SH-groups, serum, mg % | 1535 ± 64 | 263 ± 39* | 1602 ± 40 | 1554 ± 72 |
| Reduced glutathione, liver, mg % | 165 ± 6 | 60 ± 10* | 171 ± 12 | 164 ± 10 |
| Glycogen, liver, mg % | 2482 ± 99 | 739 ± 78* | 2430 ± 106 | 2691 ± 191 |
| Concentration of bromsulphalein at 10th minute after administrating the serum, extinction, | 13.7 ± 0.9 | 40.4 ± 4.2* | 13.7 ± 0.5 | 13.5 ± 1.6 |
| Ceruloplasmin, serum, mg/l | 417 ± 12 | 989 ± 81* | 453 ± 21 | 477 ± 44 |
| Cholesterol, serum, mmol/l | 1.77 ± 0.24 | 1.32 ± 0.20 | 1.79 ± 0.35 | 1.70 ± 0.19 |
| Total bilirubin, serum, mmol/l | 3.2 ± 0.4 | 7.4 ± 0.3* | 3.3 ± 0.2 | 3.8 ± 0.5 |

*statistically significant differences from intact animals at $p < 0.05$

TABLE 4

Body weight and relative liver mass of experimental animals after treatment of $CCl_4$ intoxication with the inventive substance in varying dosages, M ± m.

| Indicators | Intact | $CCl_4$ intoxication | | |
|---|---|---|---|---|
| | | No treatment | Essentiale, 100 mg/kg | The inventive substance, 90 mg/kg |
| Body weight, g | 179 ± 7 | 165 ± 10* | 176 ± 8 | 174 ± 7 |
| Relative liver mass, mg/100 g | 29.70 ± 1.46 | 41.30 ± 1.17* | 32.78 ± 1.91 | 27.87 ± 1.03* |

*statistically significant differences from intact animals at $p < 0.05$

TABLE 5

Marker biochemical and functional indices of liver condition of the experimental animals after treatment of $CCl_4$ intoxication using the inventive substance in varying dosages, $M \pm m$.

| | | $CCl_4$ intoxication | | |
|---|---|---|---|---|
| Indicators | Intact | No treatment | Essentiale 100 mg/kg | The inventive substance 90 mg/kg |
| Alanine aminotransferase, serum, μmol/(s · l) | 0.59 ± 0.04 | 1.56 ± 0.11* | 0.93 ± 0.08* | 0.85 ± 0.08 |
| Aspartate aminotransferase, serum, μmol/(s · l) | 0.35 ± 0.04 | 0.80 ± 0.07* | 0.42 ± 0.06 | 0.32 ± 0.04 |
| Alkaline phosphatase, serum, nmol/(s · l) | 852 ± 30.7 | 1677 ± 168.8* | 1070 ± 98.3* | 811 ± 26.3 |
| Hexenal sleep, min | 31.0 ± 2.0 | 59.0 ± 4.0* | 36.0 ± 2.5 | 31.0 ± 2.0 |

*statistically significant differences from intact animals at $p < 0.05$

TABLE 6

Quantitative assessment of the effectiveness of different treatment methods during toxic liver lesion caused by $CCl_4$.

| No. of item | Experimental groups | Indicators | | | | | |
|---|---|---|---|---|---|---|---|
| | | ALT | AST | ALP | Weight coefficient | Hexenal sleep | Total points |
| 1 | $CCl_4$ + the inventive substance, 180 mg/kg | 7 | 7 | 11 | 10 | 10 | 45 |
| 2 | $CCl_4$ + Essentiale, 100 mg/kg | 7 | 9 | 5 | 8 | 8 | 37 |
| 3 | $CCl_4$ (no treatment) | 4 | 2 | 1 | 1 | 5 | 13 |
| 4 | Intact | 11 | 11 | 9 | 6 | 10 | 47 |

The invention claimed is:

1. A solid reaction product comprising 1-(4-bromophenyl)-6-hydroxy-5-nitroso-1,2,3,4-tetrahydropyrimidine-2,4-dione:

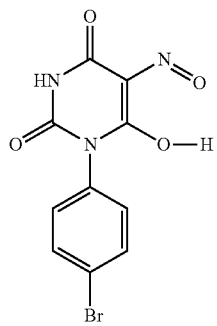 [SMILES: O=Nc1c(O)n(-c2ccc(Br)cc2)c(=O)[nH]c1=O]

or a pharmacologically acceptable salt thereof, wherein said solid reaction product has a melting point of 220° C.

2. A method for synthesizing 1 (4 bromophenyl)-6-hydroxy-5-nitroso-1,2,3,4-tetrahydropyrimidine-2,4-dione:

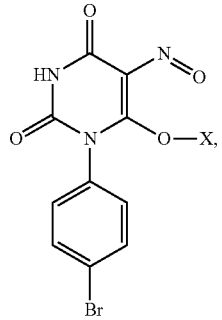

or a pharmacologically acceptable salt thereof, said method comprising the steps of:
 a. forming a solvated sodium metal by dissolving a sodium metal in anhydrous methanol;
 b. adding diethyl malonic ether to said solvated sodium metal;
 c. adding under heat and reflux N-(4-bromophenyl) urea to the diethyl malonic ether and solvated sodium metal mixture of step b;
 d. cooling the mixture of step c to 25° C. and diluting the mixture of step c with water;
 e. reacting the diluted mixture of step d with sodium nitrite to afford a clear solution;
 f. reacting the mixture of step e with acid to form a precipitate;
 g. filtering and washing said precipitate to afford (1-(4-bromophenyl)-6-hydroxy-5-nitroso-1,2,3,4-tetrahydropyrimidine-2,4-dione).

3. The solid reaction product of claim 1, wherein said pharmacologically acceptable salt is a sodium, potassium, lithium, ammonium or uronium salt.

4. The solid reaction product of claim 1, wherein said solid reaction product is a crystalline solid.

5. The solid reaction product of claim 1, wherein said solid reaction product is a purified reaction product.

6. The solid reaction product of claim 5, wherein said purified reaction product is purified by recrystallization.

7. A pharmaceutical composition comprising the solid reaction product of claim 1 and a pharmaceutically acceptable carrier or excipient.

8. The pharmaceutical composition of claim 7, wherein said composition is provided in the form of an aqueous solution.

9. The pharmaceutical composition of claim 7, wherein said composition is provided in the form of an oil suspension.

10. A method for treating a liver lesion in a subject in need thereof, comprising administering to said subject a therapeutically effective amount of the pharmaceutical composition of claim 7.

11. The method of claim 10, wherein the liver lesion was caused by a chemical or biological agent.

12. A method for treating a liver cirrhosis in a subject in need thereof, comprising administering to said subject a therapeutically effective amount of the pharmaceutical composition of claim 7.

13. A method for treating a hepatitis in a subject in need thereof, comprising administering to said subject a therapeutically effective amount of the pharmaceutical composition of claim 7.

14. The method of claim 10, wherein the pharmaceutical composition is administered orally.

15. The method of claim 12, wherein the pharmaceutical composition is administered orally.

16. The method of claim 13, wherein the pharmaceutical composition is administered orally.

17. A solid reaction product comprising 1-(4-bromophenyl)-6-hydroxy-5-nitroso-1,2,3,4-tetrahydropyrimidine-2,4-dione:

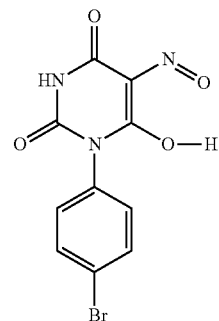 [SMILES: O=Nc1c(O)n(-c2ccc(Br)cc2)c(=O)[nH]c1=O]

or a pharmacologically acceptable salt thereof, prepared by a process comprising the steps of:
   a. forming a solvated sodium metal by dissolving a sodium metal in anhydrous methanol;
   b. adding diethyl malonic ether to said solvated sodium metal;
   c. adding under heat and reflux N-(4-bromophenyl) urea to the diethyl malonic ether and solvated sodium metal mixture of step b;
   d. cooling the mixture of step c to 25° C. and diluting the mixture of step c with water;
   e. reacting the diluted mixture of step d with sodium nitrite to afford a clear solution;
   f. reacting the mixture of step e with acid to form a precipitate;
   g. filtering and washing said precipitate to afford said solid reaction product.

18. The solid reaction product of claim 17, wherein said pharmacologically acceptable salt is a sodium, potassium, lithium, ammonium or uronium salt.

19. The solid reaction product of claim 17, wherein said solid reaction product is a crystalline solid form.

20. A pharmaceutical composition comprising the solid reaction product of claim 17 and a pharmaceutically acceptable carrier or excipient.

* * * * *

UNITED STATES PATENT AND TRADEMARK OFFICE
CERTIFICATE OF CORRECTION

| | |
|---|---|
| PATENT NO. | : 8,999,959 B2 |
| APPLICATION NO. | : 13/883854 |
| DATED | : April 7, 2015 |
| INVENTOR(S) | : Viktor Veniaminovich Tets, Georgy Viktorovich Tets and Konstantin Andreevich Krasnov |

It is certified that error appears in the above-identified patent and that said Letters Patent is hereby corrected as shown below:

In the Claims

Column 12, Lines 20-21, In Claim 2, please replace "1 (4 bromophenyl)-6-hydroxy-5-nitro so-1 ,2,3,4-tetrahydropyrimidine-2,4-dione" with "1-(4-bromophenyl-6-hydroxy-5-nitroso-1,2,3,4-tetrahydropyrimidine-2,4-dione."

Column 12, Lines 22-35, In Claim 2, please replace the structure:

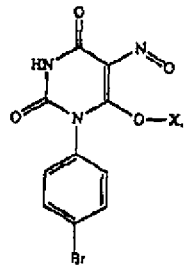   with

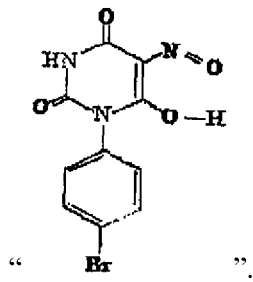  " ".

Signed and Sealed this
Seventh Day of July, 2015

Michelle K. Lee
*Director of the United States Patent and Trademark Office*